(12) United States Patent
Paturu (10) Patent No.: US 6,589,159 B2
(45) Date of Patent: Jul. 8, 2003

(54) MAGNETIC THERAPY DEVICES AND METHODS

(76) Inventor: Sumathi Paturu, 307 Brooke-Lyn Ter., Pleasant Grove, AL (US) 35127

( * ) Notice: Subject to any disclaimer, the term of this patent is extended or adjusted under 35 U.S.C. 154(b) by 0 days.

(21) Appl. No.: 09/834,436

(22) Filed: Apr. 12, 2001

(65) Prior Publication Data

US 2002/0151759 A1 Oct. 17, 2002

(51) Int. Cl.[7] ................................................. A61N 1/00
(52) U.S. Cl. ......................................................... 600/15
(58) Field of Search ................................... 600/9–15

(56) References Cited

U.S. PATENT DOCUMENTS

| 125,006 A | 3/1872 | Bazault |
| 237,939 A | 2/1881 | Wilson |
| 1,050,280 A | 1/1913 | Krugger |
| 1,394,810 A | 10/1921 | Craddock |
| 1,421,516 A | 7/1922 | Maeshima |
| 4,005,699 A | 2/1977 | Bucalo |
| 5,017,185 A | 5/1991 | Baermann |
| 5,950,239 A | 9/1999 | Lopez |
| 5,965,276 A | 10/1999 | Shlenker et al. |
| 5,984,854 A | 11/1999 | Ishikawa et al. |
| 6,023,640 A | 2/2000 | Ross |
| D431,865 S | * 10/2000 | Norton et al. ............. D24/143 |
| 6,348,033 B1 | * 2/2002 | Catlett .......................... 600/15 |

FOREIGN PATENT DOCUMENTS

| JP | 06-038997 | * 2/1994 | .................. 600/15 |
| JP | 08-10279 | * 1/1996 | .................. 600/15 |

* cited by examiner

Primary Examiner—Samuel G. Gilbert

(57) ABSTRACT

Static and electromagnetic therapeutic devices are disclosed for increasing the blood circulation to areas of the body subject to magnetic field induction. The therapeutic devices are useful in the treatment of various diseases and aliments of the human body, such as erectile dysfunction, peripheral vascular disease, cerebral insufficiency and certain vascular pathologies. The disclosure contemplates that the beneficial effects of the induced magnetic fields are the result of the interaction of certain constituents of the blood with the magnetic fields.

4 Claims, 9 Drawing Sheets

MAGNETIC THERAPY DEVICES AND METHODS

BACKGROUND

This invention relates generally to the use of magnets in the treatment of human diseases and ailments and devices for carrying out this treatment.

The study of magnetic therapy to treat human disease can be traced back as far as the early 16th century. Over the years, magnetic therapy has been alleged as a cure for diverse diseases and ailments ranging from cancer to chronic pain. The popularity of magnetic therapy continues today. However, despite the prevalence and popularity of magnetic therapy treatments, the physiological effects of magnetic therapy is still unsettled.

Magnetic fields have been historically described in relation to electric current. This relationship to electric current forms the basis of understanding the properties of magnets. All atoms are composed of protons and neutrons, which reside in the nucleus of the atom, and electrons which move rapidly about the nucleus of the atom. As the electrons are negatively charged, each electron generates its own magnetic moment, or magnetic dipole. These magnetic dipoles can be oriented in either of two opposing directions. However, not all atoms demonstrate magnetic properties. This is because many atoms have electrons that are paired with electrons of opposite magnetic dipoles, the net effect being the cancellation of the magnetic dipoles. These atoms are referred to as diamagnetic. Other atoms have unpaired electrons and possess a net magnetic dipole. These atoms do exhibit magnetic properties and are referred to as paramagnetic. Iron is an example of a paramagnetic atom. However, in some cases, the individual magnetic dipoles behave cooperatively and align themselves in the same direction to form magnetic domains. The compounds composed of these atoms demonstrate strong magnetic properties and are referred to as ferromagnetic. Ferromagnetic compounds include iron, cobalt, nickel, samarium, dysprosium and gadolinium.

Magnets always exist as dipoles, with a north pole and a south pole. Magnetic field lines emerge from the north pole and converge at the south pole. The force of a magnetic field line is known as the magnetic flux and is measured in weber (w). The strength of a magnetic field, or magnetic flux density, is the number of magnetic field lines passing through a unit area and is measured in Telsa (T), or gauss (g).

There are two types of magnetic therapy: electromagnetic therapy and static magnetic field therapy. The types of magnetic fields generated in each of these types of therapy can be different. For example, electromagnetic therapy can employ a pulsating magnet field which allows the strength of the magnetic field to be regulated by controlling the flow of current, while in a static magnetic field the strength of the magnetic field does not vary. Electromagnetic therapy is based on the principle discovered by Michael Faraday that described the relationship between the movement of a magnetic and an electric field (electromagnetic induction). Faraday observed that passing a magnet in and out of a conducting electric coil produced voltage.

It has been known for some time that electrical activity in some form is involved in many aspects of human physiology. For instance, electrical activity has been measured during the regeneration of bone. In addition, it is well documented that many cellular responses are dictated by electrical gradients generated in the cell (for example, nerve cells). Therefore, it is possible that exposure of the human body to an pulsating electromagnetic field could produce a beneficial physiological response in the body. In fact, several studies have shown beneficial effects of pulsating electromagnetic field therapy in stimulating osteogenesis. The U.S. Food and Drug Administration has recently approved the use of pulsating electromagnetic field therapy for the treatment of some types of bone fractures Various mechanism have been proposed for the effects of static magnetic field therapy, but none have achieved widespread acceptance. However, whatever the mechanism, the beneficial effects of static magnetic field therapy are most often cited to be the result of increased blood flow to the area of the body treated with the static magnetic field.

BRIEF DESCRIPTION OF THE DRAWINGS

The following embodiments of the disclosure are explained by the drawings and disclosure that follows.

DETAILED DESCRIPTION

Magnetic therapy is a widely practiced and growing alternative treatment for many diseases and ailments in Asia, Europe and North America. Although many double blind clinical studies have documented the beneficial effects of various types of magnetic therapy, there is no satisfactory scientific mechanism for these beneficial effects.

It is well established that magnets can attract various types of metals, including iron. In the body, iron is prevalent in many places, including the blood. Blood cells contain hemoglobin molecules. Hemoglobin molecules function to transport oxygen from the lungs to the tissues of the body. Hemoglobin is composed of four subunits, with each subunit containing one molecule of iron, for a total of four iron molecules per hemoglobin molecule. Iron is paramagnetic. As a result, iron possesses a weak magnetization in the direction of an induced magnetic field. In addition, there are other paramagnetic materials present in the blood, including oxygen, sodium and potassium.

The body of a 70 kg man contains approximately 4 grams of iron, with 65%, or about 2.6 grams, being present in the hemoglobin. Therefore, hemoglobin molecules in the blood may contain enough iron to make the red blood cells of the blood responsive to magnetic fields and move, or be pulled, in the direction of an applied magnetic field.

Without being limited to other possible theories, the disclosure contemplates that the therapeutic benefits of static magnetic therapy and electromagnetic therapy that have been observed are mainly the result of increasing the blood circulation in the areas affected by magnetic induction through the attraction of the iron molecules in the hemoglobin molecules. This increased blood circulation may be the result of the attraction of the hemoglobin in the oxygen bound state or the oxygen free state.

In order to demonstrate the affinity of blood cells to magnetic fields, the disclosure has noted a uniquely suitable clinical issue for preliminary study. The penis is a profoundly vascularized organ. In the penis, blood flows into sponge like sinusoids rather than capillary like tubes. In addition, the penile circulation is isolated from the circulation of the body. Therefore, the circulation in the penis can be readily observed without the use of sophisticated radiological devices, and the effects of magnetic induction on the circulation can be observed.

Figure 1:
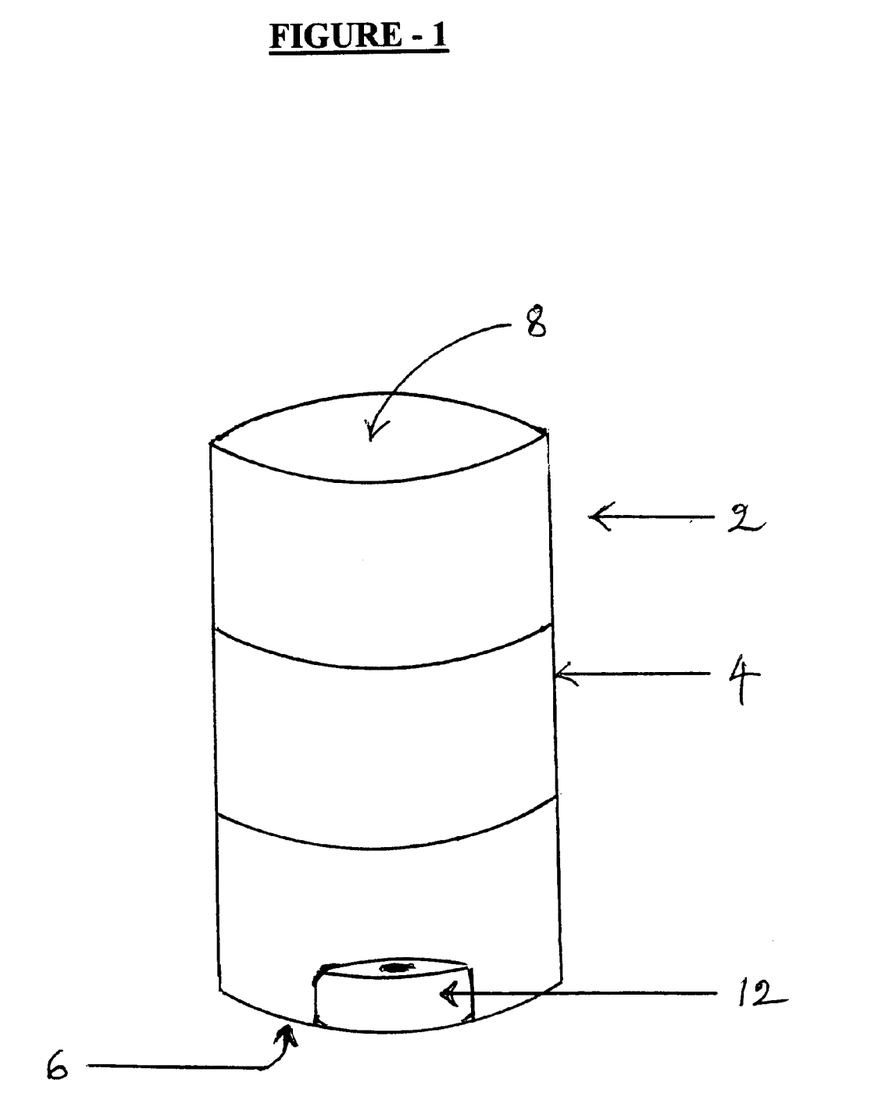
FIG. 1 is a full frontal view of an embodiment of a magnetic therapy device to treat erectile dysfunction.

Preliminary evaluation was performed on four human subjects to study the effects of magnetic fields on blood circulation in the penis. Initial studies were conducted using a static magnetic field, but the disclosure should not be read so as to prohibit use of pulsed electromagnetic fields. An embodiment of the device used in the initial studies is shown in FIG. 1. The device 2 has a tubular structure comprising a continuos side wall 4 extending the length of the device 2, one closed end 6 and one open end 8 opposite the closed end 6. The length and diameter of the device 2 can be adjusted, depending on the requirements of the user. The side wall 4 in this embodiment is comprised of a magnetic material to provide a magnetic field along the axial length of the penis when the penis is inserted into the device 2. The magnetic material comprising the side wall 4 may be may be of any suitable composition, but in this embodiment it is a flexible, rubber magnetic material. A tip magnet 12 is also shown on the interior surface of the closed end 6 with the magnetic field facing the tip of the penis. The tip magnet 12 may be of any composition, but in this embodiment the tip magnet 12 is a button Alnico magnet, which is formed from an alloy of iron, cobalt, aluminum and nickel. A plurality of magnets may be employed. The strength of the magnetic field generated by the magnetic side wall 4 and the tip magnet 12 is such that the magnetic field is effective in increasing blood circulation in the penis and causing an erection (defined as partial or complete engorgement of the penis). The tip magnet 12 may be of higher strength than the magnetic material comprising the side wall 4. In the embodiment shown in FIG. 1 the tip magnet 12 has a strength of 1250 gauss. The device 2 is secured together by any convenient means, such as casting plaster.

Other embodiments of the device 2 are possible. For instance, the device 2 may comprise only the tip magnet 12 with the side wall 4 being comprised of a non-magnetic material. Alternatively, the device 2 may comprise only a side wall 4 of magnetic material. In addition, the side wall 4 may be constructed such that only discrete portions of the side wall 4 contain magnetic material, for use with or without the tip magnet 12. For instance, the magnetic material in the side wall 4 may be placed such that it overlays all or some of the major veins and arteries of the penis.

The penis is inserted into the device 2. The tip of the penis should be placed in close proximity to the tip magnet 12 so that the magnetic field of the tip magnet 12 may exert the maximal pull of the blood towards the tip of the penis, and therefore, through the entire length of the penis. In the initial studies, use of the device for less than 5 minutes was sufficient to achieve penile erection. In several instances, penile erection was observed in time spans less than 1 minute. Additional device can be used to maintain venous occlusion for sustained erection, such as a band like structure encircling the base of the penis.

Figure 2:
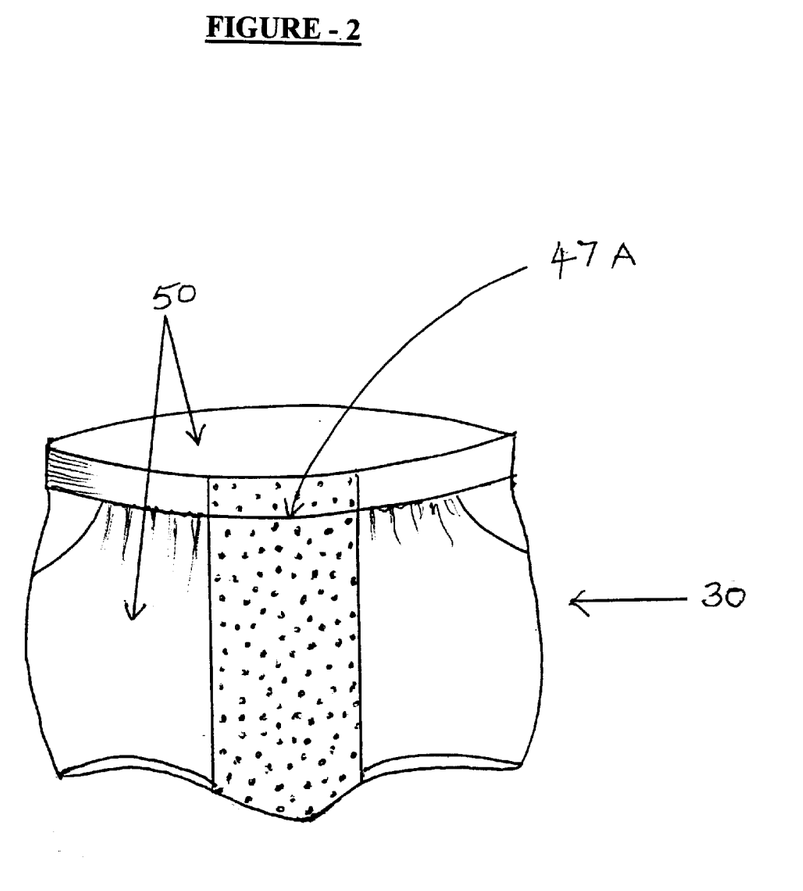
FIG. 2 is a full frontal view of an embodiment of an undergarment capable of receiving a magnetic therapy device.
Figure 3:
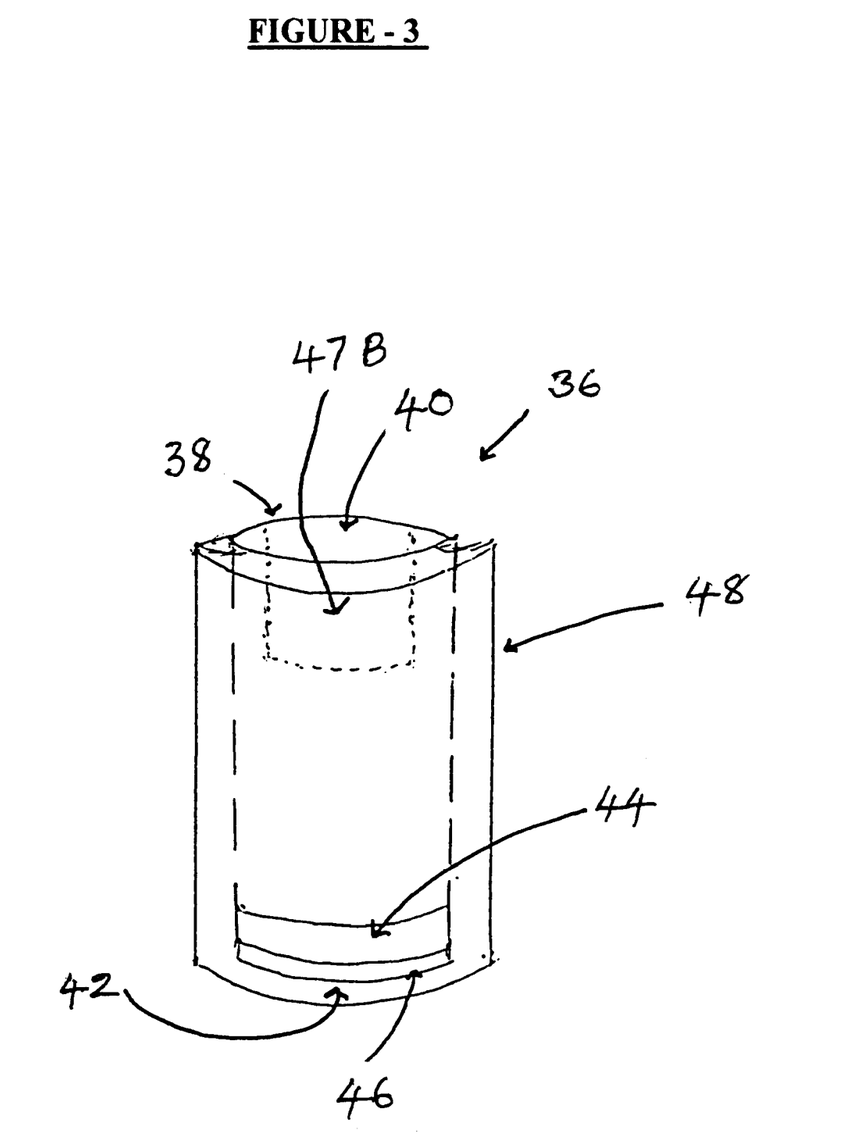
FIG. 3 is a full frontal view of an embodiment of a magnetic therapy device suitable for use with the undergarment illustrated in FIG. 2.

An undergarment 30 incorporating a magnetic element is also disclosed and is shown in FIGS. 2 and 3. The undergarment 30 has an interior and exterior side and may be of either brief or boxer design, with the brief design being illustrated in FIG. 2 In this embodiment, the magnetic element is a detachable pouch 36 of generally tubular shape, comprising a continuous, tubular side wall 38 forming a tubular shape, an open end 40 and a closed end 42 as shown in FIG. 3. In this embodiment, the side wall 38 is formed from flexible magnetic material, such as a thin rubber magnet. A magnet 44 is placed on the interior portion 46 of the closed end 42, with the magnetic field directed toward the open end 40. The magnet 44 may have a steel backing 46 in order to increase the magnetic field strength of the magnet in the direction of the first end 40.

The pouch 36 can be manufactured in various lengths and diameters depending on the requirements of the user (i.e. depending of the pre-erection size of the penis). Whatever size is selected, it is important that the tip of the penis be in close proximity to the magnet 44 in order for the magnet field produced by the magnet 44 to exert the greatest possible pull on the blood through the length of the penis, which results in engorgement and erection of the penis. In initial experiments, the magnet 44 had a field strength of about 1000 gauss.

Figure 4:
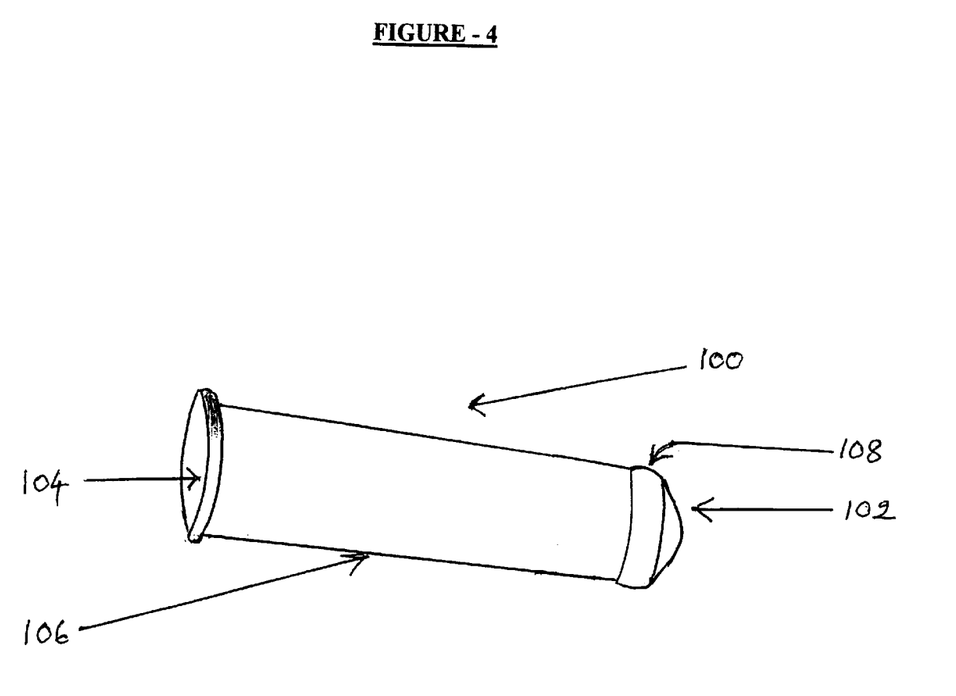
FIG. 4 is a full frontal view of an embodiment of a magnetic condom.

The interior side of the undergarment 30 and the pouch 36 incorporate complementary fastening elements 47A and 47B, allowing the pouch 36 to be removably attached to the undergarment 30. In FIGS. 3 and 4, the complementary fastening elements 47A and 47B are velcro patches, but other embodiments are possible, such as buttons, snaps, zippers, etc. In FIG. 2, the fastening element 47A extends along the length of the front section 50 of the undergarment 30, allowing the user to adjust the height of the pouch 36 as desired. As the pouch 36 is removable from the undergarment 30, different size combinations of the pouch 36 and undergarment 30 can be offered, with the size of the pouch 36 and undergarment 30 being dictated by the requirements of the user.

In an alternate embodiment, the pouch 36 may incorporate a sheath of steel foil 48 or similar material on the side of the pouch 36 opposite the complementary fastening element 47B. The function of the sheath 48 is to prevent the magnetic field generated by the magnetic side wall 38 and magnet 44 from producing engorgement and erection of the penis when not desired. When engorgement and erection of the penis is not desired, the penis is removed from the pouch. As such, the penis is effectively shielded from the magnetic fields produced by the side wall 38 and magnet 44.

In an alternate embodiment, the pouch 36 comprises a continuous side wall 38 forming a tubular shape, an open first end 40 and a closed second end 42 as shown in FIG. 3. However, in this embodiment, the side wall 38 is formed from any non-magnetic material instead of the flexible magnetic material described above. The magnet 44 is retained on the interior portion of the closed second end 42, with the magnetic field directed toward the open first end 40. In addition, the pouch 36 may comprise the side wall 38 comprising magnetic material, but omit the magnet 44. In addition, the side wall 38 may be constructed such that only discrete portions of the side wall 38 contain magnetic material, for use with or without the magnet 44. For instance, the magnetic material in the side wall 38 may be placed such that it overlays all or some of the major veins and arteries of the penis.

The undergarment 30, a pocket is placed on undergarment 30 for storage of the pouch 36 when not in use. The pocket may have a complementary fastening element to mate with the fastening element 47B on the pouch 36.

As shown in FIG. 4, a magnetic condom 100 is also disclosed. The magnetic condom 100 is of typical construction, comprising a closed tip end 102 and an open end 104, the closed end 102 and the open end 104 being joined by a continuous, tubular side wall 106. The side wall 106 and closed end 102 comprise a thin, durable rubber material in which magnetic particles have been embedded. In this embodiment, the condom 100 also incorporates a ring 108 of magnetic material a few millimeters from the closed end 102 for increased pull of blood to the tip of the penis and throughout the length of the penis. The magnetic material incorporated into the side wall 106 and the ring 108 may be of any effective composition. The strength of the magnetic field created by the side wall 106 and the ring 108 is such that the magnetic field is effective in increasing the blood circulation to the penis. In alternate embodiments, the condom 100 may incorporate magnetic material only in the side wall 106, or only in the ring 108 of condom 100. The condom 100 can be used during intercourse for sustained erection. In severe cases of erectile dysfunction, the condom 100 can be used in conjunction with the device 2 and/or the undergarment 30.

The beneficial effects of magnetic therapy on the blood circulation also has implications that extend to other clinical conditions that are vascular in origin, such as peripheral vascular disease of the legs and feet. Peripheral vascular disease of the lower extremities is commonly found in people suffering from diabetes. A magnetic boot (which for the purpose of specification shall include all types of footwear) for use in the treatment of peripheral vascular disease of the legs and feet is disclosed and shown in FIG. 5. Through the effect of the magnetic field, blood is attracted to the periphery of the legs and feet, thereby increasing peripheral circulation.

Figure 5:
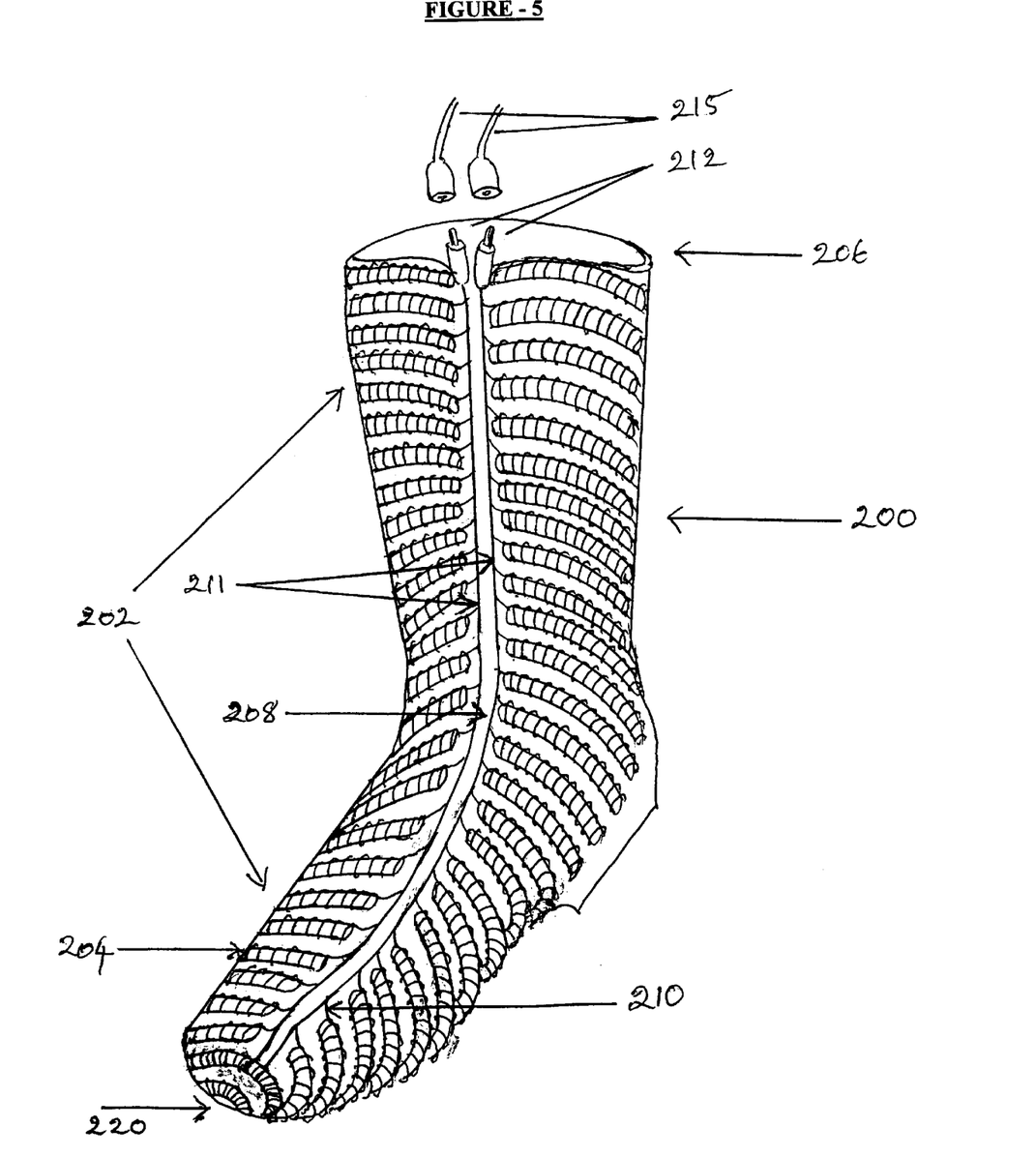
FIG. 5 is a full frontal view of an embodiment of a magnetic boot.

The boot 200 is composed of a frame 202. The frame 202 is itself composed of individual frame members 204 secured together and a rim 206. The frame 202 is not completely closed, but is constructed so as to produce an opening 208 in the frame 202. The opening 208 is located on the top of the boot 200 and the opening extends substantially the entire length of the boot 200. The opening 208 allows the user to easily place his foot and/or lower leg into the boot, and provides a comfortable fit and wear to those who suffer from peripheral vascular disease. The frame 202 of the boot 200 can comprise either a magnetic material if static magnetic therapy is desired, or can comprise a malleable iron material if pulsed electromagnetic therapy is desired. The strength of the magnetic field created is such that the magnetic field is effective in increasing peripheral blood circulation.

Figure 6:
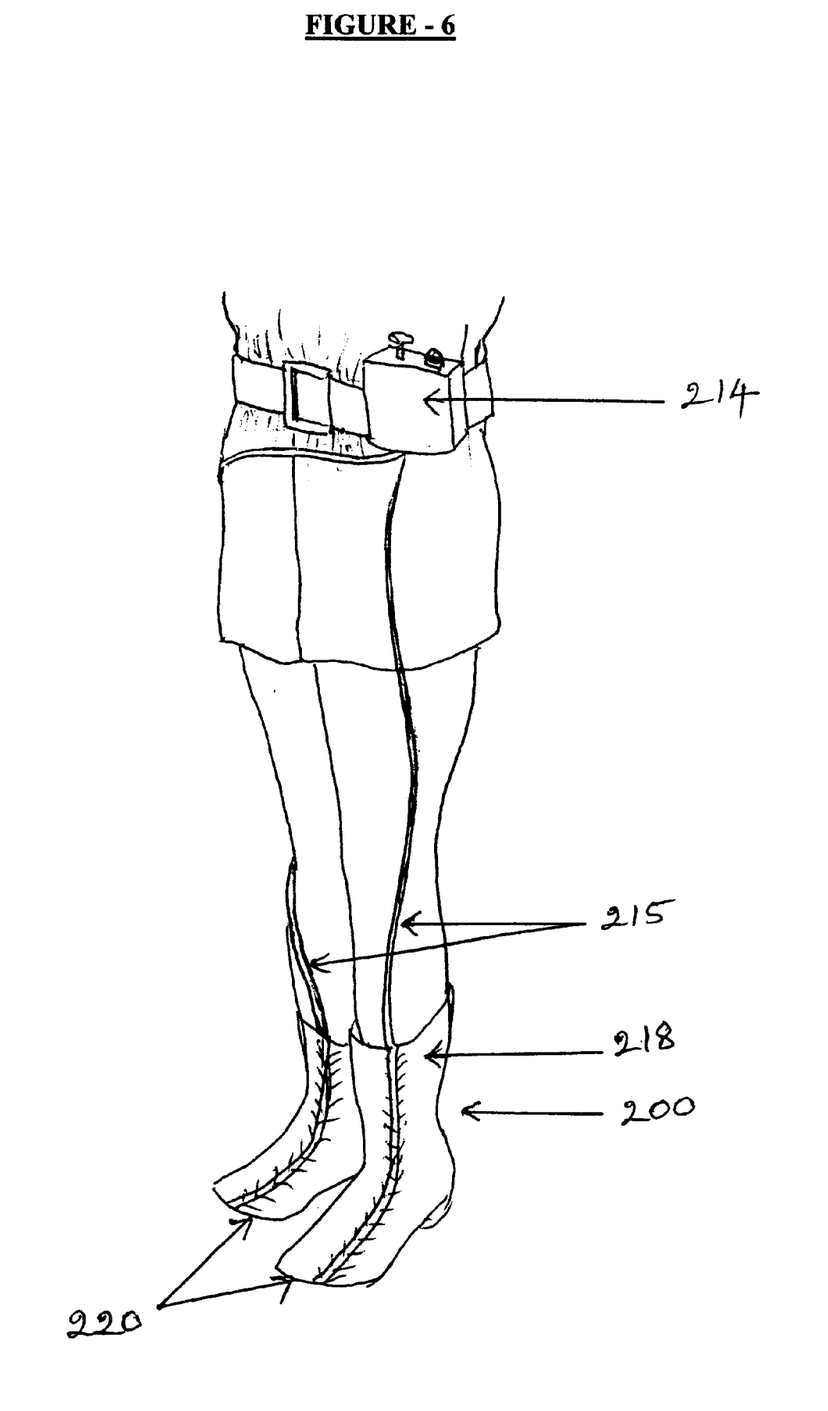
FIG. 6 is a full frontal view of the an embodiment of the magnetic boot illustrating the connection to an electrical source.

In the case where pulsed electromagnetic therapy is desired, electrical conducting wires 210 are wrapped around the individual frame members 204. The wires 210 extend into the opening 208 where they join main conducting wires 211 which terminate at two electrical connectors 212 secured to the rim 206. The wires 210 and 211 are connected to an adjustable electrical source 214 through electrical cables 215, as illustrated in FIG. 6. The electrical source can activate the electric circuit by allowing electric current to flow through the cables 215 and the wires 210 and 211. Each time an electrical circuit is activated, an electromagnetic field is created around the foot and/or lower leg of the wearer. The frame members 204 function as solenoid due to the effect of the electrical current carried through the wires 210 and increase the magnetic field generated in the wires 210. The electrical source 214 is compact enough so that it can be conveniently carried by the user. No matter whether static or electromagnetic therapy is involved, the boot 200 has a well insulated inner layer (not shown) and outer layer 218, with the frame 202 and wires 210 and 211 being located between the inner layer and the outer layer 218.

The electrical source 214 can be adjusted so that the electrical circuit formed by the wires is activated in discrete temporal patterns. The electrical source 214 may be programmed to deliver electrical pulses which are timed with the user's pulse. For example, a pulse sensor (not shown) may be attached in the groin region of the user such that it can detect the femoral pulse. Each time a femoral pulse is detected, the electrical source 214 is activated, sending electrical current to the wires 210 and 211, thereby inducing an electromagnetic field around the lower legs and/or feet of the user. As discussed above, each time a magnetic field is created, the magnetic field attracts blood cells to the peripheral circulation (which consists largely of capillary beds that have been narrowed due to disease or other factors). When the magnetic fields are activated in coordination with the pulse of the user, the pulling effect of the magnetic field is added to the pushing effect from the pressure of the proximal circulation, resulting in increased blood circulation to the periphery. Also, since the magnetic field attracts the blood cells in coordination with the natural circulation, the blood flow is allowed to enter the venules and into the venous circulation after the plateau of the pulse without the interference of the magnetic field. Therefore, the pulsing of the magnetic field in coordination with the pulse of the user will diminish the possibility of clot formation which may be possible when a continues magnetic field is applied.

It would also be beneficial if the magnetic field was the strongest at the tip 220 of the boot 200 near the toes and lower foot, as the peripheral circulation in the toes and/or lower foot are often the first and most severely affected areas. A stronger magnetic field can be created by increasing the density of the wires 210 around the frame members 204 forming the tip 220 of the boot 200. It may also be desired to increase the strength of the magnetic field along the course of the major arteries, such as the doorsills pedis artery and the posterior tibial artery. In this case, the density of the wires 210 could be increased along the course of the desired artery.

Figure 7:
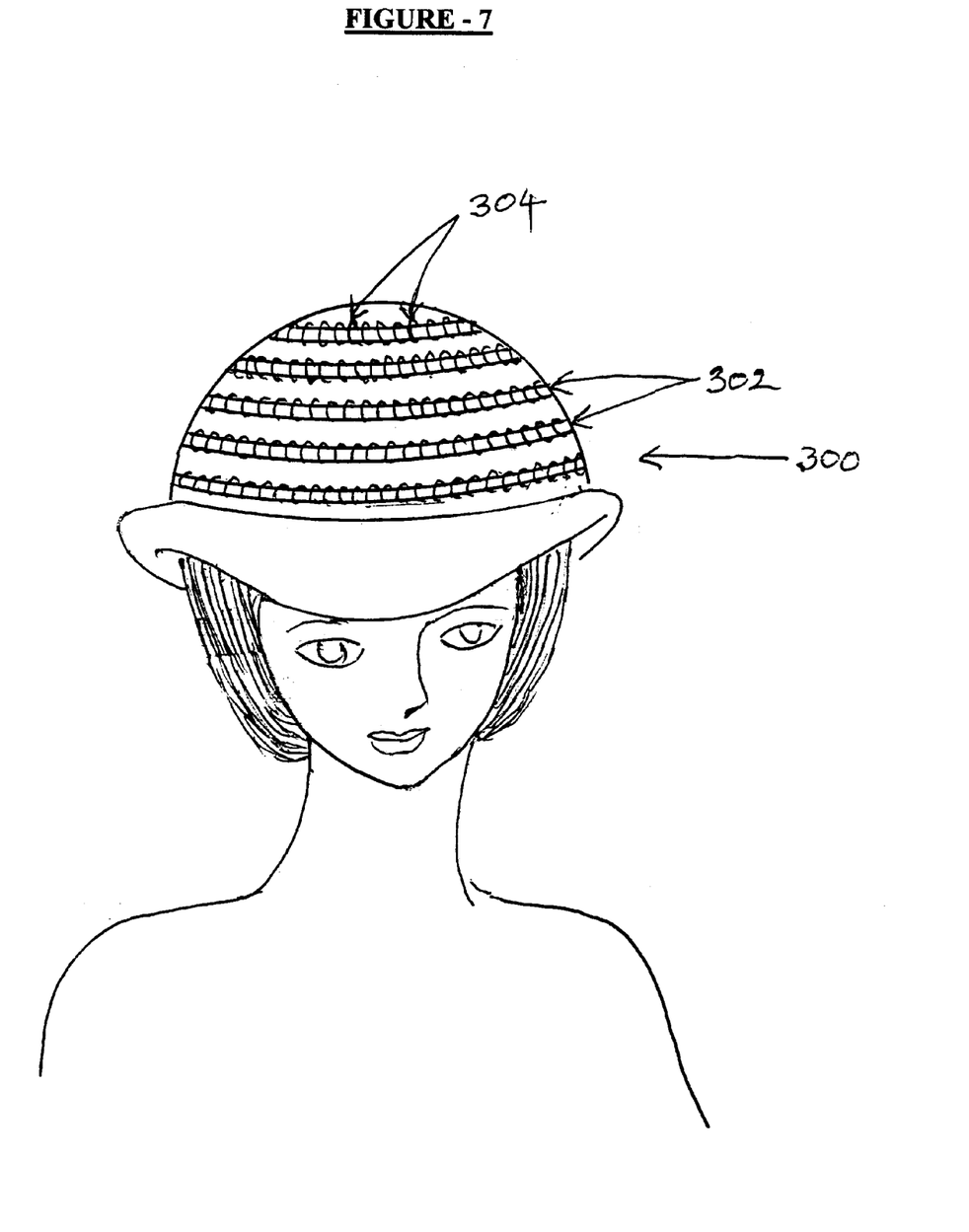
FIG. 7 is a full frontal view of an embodiment of a magnetic headpiece.

Cerebral vascular insufficiency can also be treated with magnetic therapy. Cerebral vascular insufficiency is often due to atherosclerosis caused by local thrombotic pathology with threatened cerebral infarct or actual cerebral infarct. For generalized cerebral vascular insufficiency, a magnetic headpiece 300 can be used, as illustrated in FIG. 7. The magnetic field generated by the headpiece 300 can be either a continuos static magnetic field or a pulsed electromagnetic field. In either case, strong magnetic fields (on the order of 1000–2000 gauss) will be preferred in order to penetrate the bones of the skull. The magnetic field can be arranged in any useful configuration, such as a spiral or concentric circles.

FIG. 7 illustrates an embodiment of the headpiece 300 incorporating electromagnets. Headpiece conducting members 302 are arranged about and secured to the headpiece 300 in any effective configuration (FIG. 7 shows the headpiece conducting members 302 arranged in concentric circles). Electrical conducting wires 304 are wrapped around the headpiece conducting members 302. As noted above, the strength of the magnetic field produced can be varied by varying the density of the wires 304. The wires 304 are connected to an electrical source (not shown) as discussed above in regards to the magnetic boot 200. In addition, the electrical source can be connected to a pulse sensor to control the induction of the magnetic field in coordination with the natural pulse of the user to attain the benefits discussed above.

Figure 8:
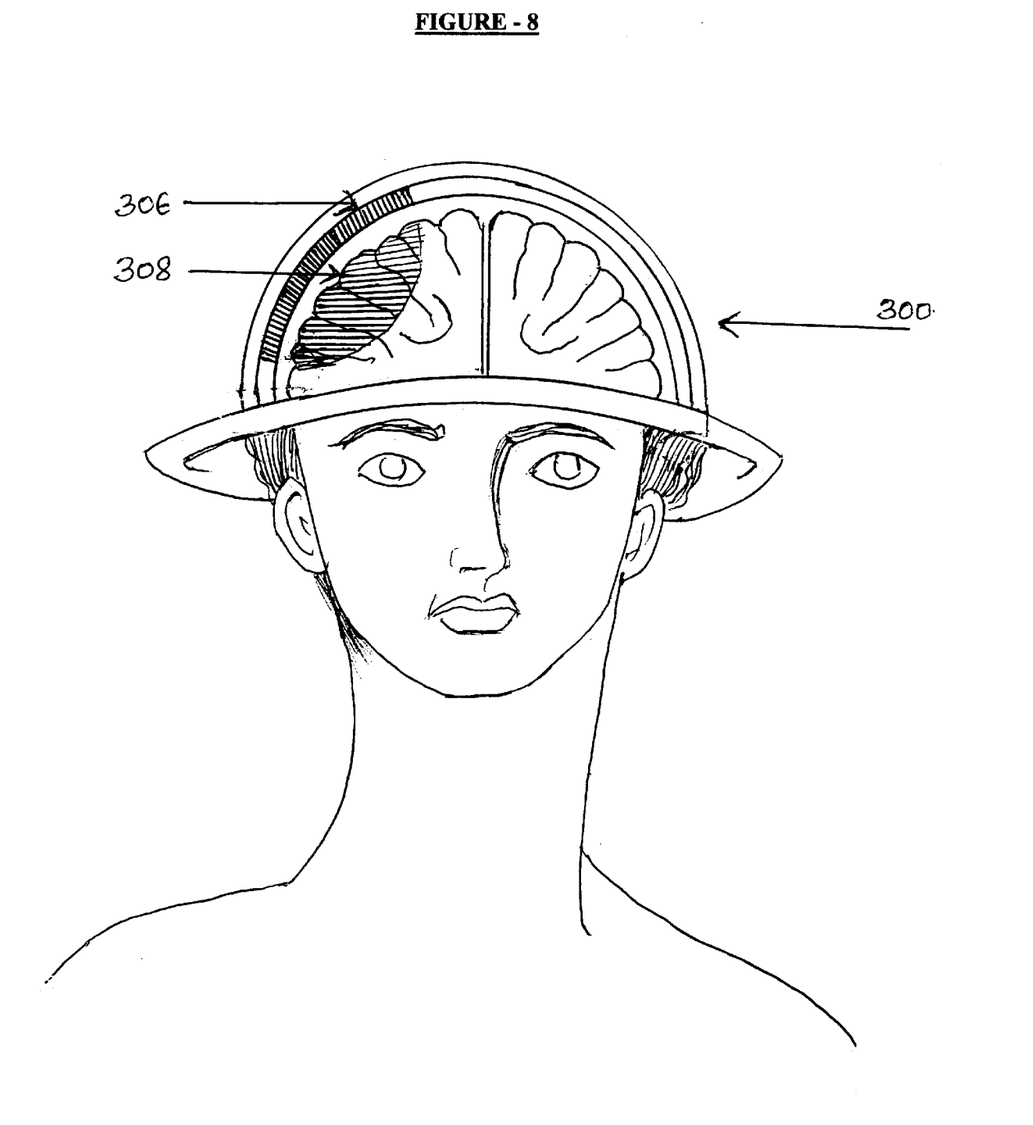
FIG. 8 is a full frontal view of an embodiment of a magnetic headpiece for treating localized regions of the head.

For patients with localized thrombosis and/or threatened or actual infarct of the brain 308, the magnetic field can be localized to prevent Steel syndrome which is a possible complication with generalized magnetic fields. An embodiment of the headpiece 300 illustrating this principle is shown in FIG. 8. The magnetic field can be localized over an effected region in the brain by any convenient means, such as the attachment of a magnetic patch 306 applied to the inner lining of the headpiece 300. The magnetic patch 306 can be attached by any means, such as velcro. By localizing the magnetic field to the region of the brain with vascular insufficiency, blood circulation can be increased in these regions by the principles discussed above Magnetic therapy may also be applicable to treatment of vascular pathology. Examples of such vascular pathology include those associated with coronary or other atherosclerotic or thrombotic areas with blockage, balloon angioplasty and placement of stents.

Figure 9:
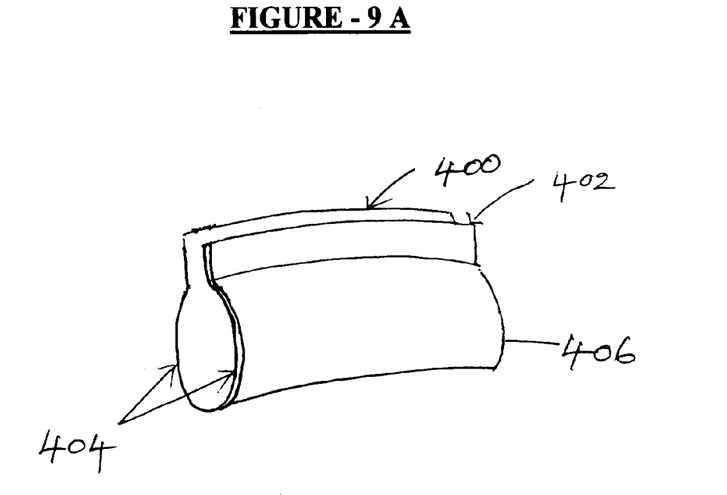
FIG. 9A is a full frontal view of an embodiment of a magnetic device useful for treating various vascular pathology.
FIG. 9B is a full frontal view of an embodiment of a magnetic device useful for treating vascular pathology caused by the insertion of a stent.

FIGS. 9A and 9B show an embodiment of a device used in the treatment of vascular pathology. In this embodiment, the device is a magnet 400 which is applied around the artery 401 distal to the area of pathology 402 or the area where a stent 404 is placed. The magnet 400 is preferably composed of a flexible material, such as rubber. The magnet 400 is wrapped around the artery 401 at the desired locations, and secured in place by joining the opposite ends of the magnet 400 together to create seel 406. In this manner the magnet 400 forms a tube like structure around the artery. This can be accomplished by any convenient means, such as cauterization or stapling. The strength of the magnet 400 is such that the magnetic field produced is effective in drawing the circulation away from the area of pathology 402 or stent 404. The magnet 400 can be of various lengths, depending on the strength of the magnetic field desired, and other factors.

Due to the placement of the magnet 400 distal to the area of pathology 402 or stent 404, the blood that flows into these areas is attracted to the magnetic field and is pulled distal to the area pathology 402 or stent 404, so that the blood flow does not become stagnant and initiate further thrombosis at the area of pathology 402 or the stent 404. The magnet 400 can be placed around the artery during surgical procedures designed to treat the pathology or insert the stent 404, or can be applied with an instrument similar to the endoscope.

The description is intended to be illustrative of the construction blocks and system of construction described herein. It should be appreciated that various modifications could be made in the construction blocks, gaskets and system of construction utilizing the construction blocks and gaskets which remain within the scope and teaching of the instant disclosure. The details given herein are to be interpreted as illustrative only and not in a limiting sense.

What is claimed:

1. A therapeutic device for creating a magnetic field in and around a penis, the device comprising:
   a. a closed end, the closed end further comprising an inner and an outer surface, an open end and a side wall, the side wall joining the closed end and the open end together to create a pocket of generally tubular shape defined by the side wall and the closed end; and
   b. at least one tip magnet placed on the inner surface of the closed end with the magnetic field directed toward the open end of the device.

2. The device of claim 1 where the strength of the magnetic field produced by the at least one tip magnet is effective in increasing blood circulation in the penis and causing an erection.

3. The device of claim 2 where the at least one tip magnet produces a magnetic field strength greater than 1250 gauss.

4. The device of claim 1 wherein the side wall is comprised of a magnetic material.

* * * * *